US011071520B2

(12) United States Patent
Sandhu et al.

(10) Patent No.: US 11,071,520 B2
(45) Date of Patent: Jul. 27, 2021

(54) TISSUE IMAGING AND ANALYSIS USING ULTRASOUND WAVEFORM TOMOGRAPHY

(71) Applicant: Delphinus Medical Technologies, Inc., Novi, MI (US)

(72) Inventors: Gursharan Singh Sandhu, Novi, MI (US); Nebojsa Duric, Novi, MI (US); Cuiping Li, Novi, MI (US); Olivier Roy, Novi, MI (US); Erik West, Novi, MI (US)

(73) Assignee: Delphinus Medical Technologies, Inc., Novi, MI (US)

( * ) Notice: Subject to any disclaimer, the term of this patent is extended or adjusted under 35 U.S.C. 154(b) by 521 days.

(21) Appl. No.: 15/909,661

(22) Filed: Mar. 1, 2018

(65) Prior Publication Data

US 2018/0185005 A1 Jul. 5, 2018

Related U.S. Application Data

(63) Continuation of application No. PCT/US2016/050014, filed on Sep. 1, 2016.
(Continued)

(51) Int. Cl.
*A61B 8/13* (2006.01)
*A61B 8/00* (2006.01)
(Continued)

(52) U.S. Cl.
CPC ............. *A61B 8/13* (2013.01); *A61B 8/085* (2013.01); *A61B 8/0825* (2013.01); *A61B 8/15* (2013.01);
(Continued)

(58) Field of Classification Search
None
See application file for complete search history.

(56) References Cited

U.S. PATENT DOCUMENTS

2006/0106307 A1 5/2006 Dione et al.
2008/0269613 A1* 10/2008 Summers ............... A61B 8/483
600/459
(Continued)

FOREIGN PATENT DOCUMENTS

WO WO-2017040866 A1 3/2017

OTHER PUBLICATIONS

Kim et al. ("Analysis of inverse scattering solution from single frequency, combined transmission and reflection data for the Helmholtzand Riccati exact wave equations"; Acoustical imaging; pp. 359-369, vol. 15; 1986).*
(Continued)

*Primary Examiner* — Oommen Jacob
*Assistant Examiner* — Shahdeep Mohammed
(74) *Attorney, Agent, or Firm* — Wilson Sonsini Goodrich & Rosati

(57) ABSTRACT

This application presents a system and related methods that analyze a volume of tissue using ultrasound waveform tomography imaging. By using frequency-domain waveform tomography techniques and a gradient descent algorithm, the system can reconstruct the sound speed distributions of a volume of tissue, such as breast tissue, of varying densities with different types of lesions. By allowing sound speed to have an imaginary component that characterizes sound attenuation, the system can classify the different types of lesions with a fine granularity.

16 Claims, 6 Drawing Sheets

Related U.S. Application Data

(60) Provisional application No. 62/294,360, filed on Feb. 12, 2016, provisional application No. 62/212,983, filed on Sep. 1, 2015.

(51) Int. Cl.
    *G06T 11/00*     (2006.01)
    *A61B 8/15*     (2006.01)
    *A61B 8/08*     (2006.01)
    *G06T 11/40*     (2006.01)

(52) U.S. Cl.
CPC ............ *A61B 8/406* (2013.01); *A61B 8/4209* (2013.01); *A61B 8/483* (2013.01); *A61B 8/485* (2013.01); *A61B 8/52* (2013.01); *A61B 8/5223* (2013.01); *G06T 11/003* (2013.01); *G06T 11/40* (2013.01); *A61B 8/4281* (2013.01); *A61B 8/4483* (2013.01); *A61B 8/463* (2013.01); *A61B 8/466* (2013.01)

(56) References Cited

U.S. PATENT DOCUMENTS

| | | | |
|---|---|---|---|
| 2013/0041261 A1* | 2/2013 | Li | A61B 8/0825 600/442 |
| 2014/0066760 A1* | 3/2014 | Duric | A61B 8/085 600/431 |
| 2014/0364736 A1* | 12/2014 | Huang | G01S 15/8997 600/447 |
| 2015/0025388 A1 | 1/2015 | Huang et al. | |

OTHER PUBLICATIONS

Sandhu et al. ("Frequency domain ultrasound waveform tomography: breast imaging using a ring transducer", Institute of physics and engineering in medicind; Phys. Med. Biol. 60 (Jun. 2015); pp. 5381-5398).*
Aki, et al., Quantitative seismology, 2002, vol. 1.
Chang et al. Reconstruction of ultrasonic sound velocity and attenuation coefficient using linear arrays: Clinical assessment. Ultrasound in medicine & biology, 33(11),1681-1687 (2007) doi:10.1016/j.ultrasmedbio.2007.05.012.
Desantis, et al., Breast Cancer Statistics, 2011., CA Cancer J. Clin. 61(6):409-18 (2011).
Duck, Physical properties of tissues: a comprehensive reference book, 2013, Academic press.
Duric et al., "Detection of Breast Cancer with Ultrasound Tomography: First Results with the Computed Ultrasound Risk Evaluation (CURE) Prototype," Med Phys, 34(2), (2007).
Durick, et al., Breast imaging with the softvue imaging system: First results. Proc. SPIE 8675, Medical Imaging 2013:Ultrasonic Imaging, Tomography, and Therapy, 86750K (Mar. 29, 2013) doi:10.1117/12.2002513 8 pages.
Edmonds, et al., Ultrasound tissue characterization of breast biopsy specimens, Ultrasonic imaging, Apr. 1991,13(2)162-185.
Goss, et al., Comprehensive compilation of empirical ultrasonic properties of mammalian tissues, The Journal of the Acoustical Society of America, 1978, 64(2), 423-457.
Gotzsche et al. Is Screening for breast cancer with mammography justifiable? The Lancet Jan. 8, 2000; 355:129-34.
Leitch et al., American Cancer Society Guidelines for the Early Detection of Breast Cancer: Update 1997., CA Cancer J. Clin. 1997; 47: 150-153.
Li et al., Comparison of Ultrasound Attenuation Tomography Methods for Breast Imaging, Medical Imaging 2008: Ultrasonic Imaging and Signal Processing, Proc. of SPIE., vol. 6920, 692015-(1-9), 2008.
Li, et al., Toward a practical ultrasound waveform tomography algorithm for improving breast imaging, Proc. SPIE 9040, Medical Imaging Mar. 20, 2014, 90401P, doi:10.1117/12.2043686.
Li et al., "Clinical Breast Imaging Using Sound-Speed Reconstructions of Ultrasound Tomography Data," Med Imaging 2008, Proc SPIE, vol. 6920, 6920009.
PCT/US16/50014 International Search Report and Written Opinion dated Nov. 17, 2016.
Pratt, et al., Sound-speed and attenuation imaging of breast tissue using waveform tomography of transmission ultrasound data, Proc. SPIE 6510, Physics of Medical Imaging, 65104S, Mar. 19, 2007, doi:10.1117/12.708789 12 pages.
Pratt, Seismic waveform inversion in the frequency domain, part 1:Theory and verification in a physical scale model, May 1999, Geophysics 64(3):888-901.
Sandhu, et al., Frequency domain ultrasound waveform tomography: breast imaging using a ring transducer, Physics in medicine and biology, Jul. 21, 2015, 60(14), 5381.
Sandhu, et al., Frequency-domain ultrasound waveform tomography breast attenuation imaging., Medical Imaging, Apr. 2016, vol. 9790, 97900C, DOI: 10.1117/12.2218374.
Sandhu et al. High-resolution quantitative whole-breast ultrasound: in vivo application using frequency-domain waveform tomography. Proc. SPIE 9419, Medical Imaging 2015: Ultrasonic Imaging and Tomography, Mar. 17, 2015, 94190D, doi:10.1117/12.2081227 9 pages.
Song, et al., Frequency-domain acoustic-wave modeling and inversion of crosshole data: Part II-inversion method, synthetic experiments and real-data results, Geophysics 60(3),796-809 (1995).
Stavros, et al., Solid Breast Nodules: Use of Sonography to Distinguish between Benign and Maliganant Lesions., Radiology 1995; 196:123-34.
Sushilov, et al., Frequency domain wave equation and its time domain solutions in attenuating media, J. Acoust. Soc. Am., Mar. 2004, 115(4), 1431-36.
Virieux, et al., An overview of full-waveform inversion in exploration geophysics, 2009, Geophysics,74(6), WCC1-WCC26, 10.1190/1.3238367.
EP16843031.2 Search Report dated Apr. 23, 2019.
Roy, et al., Sound Speed Estimation Using Wave-based UltrasoundTomography: Theory and GPU Implementation, Proc. of SPIE, 2010, vol. 7629, p. 1-12.

* cited by examiner

TISSUE IMAGING AND ANALYSIS USING ULTRASOUND WAVEFORM TOMOGRAPHY

CROSS-REFERENCE

This application is a continuation of PCT/US2016/050014 filed on Sep. 1, 2016 which claims the benefit of U.S. Provisional Patent Applications No. 62/212,983 filed on Sep. 1, 2015 and No. 62/294,360 filed on Feb. 12, 2016, which are incorporated herein by reference. This application is related to U.S. patent application Ser. No. 14/817,470, which is incorporated herein by reference.

STATEMENT AS TO FEDERALLY SPONSORED RESEARCH

This invention was made with government support under Grants R43CA171601 and R44CA165320 awarded by the National Institutes of Health (NIH) through National Cancer Institute. The Government has certain rights in the invention.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE INVENTION

Breast cancer, one of the leading causes of cancer death, has a reduced mortality rate when it is diagnosed and detected early. Breast mammography is the current standard of breast cancer screening, but it is not without problems. This has led to an interest in other methods for the detection and screening of breast cancer. By incorporating the principles of tomography with a ring ultrasound transducer array, ultrasound tomography has led to a new technique in breast imaging.

Conventional ultrasound involves emitting an acoustic wave or beam along a focused path from a source transmitter, and allowing the wave to scatter (e.g., in reflection, refraction, diffraction, transmission) from tissue or other boundaries in its path. The scattered wave returns to a surface of one or more receiving elements, which can be centered around and/or include the transmitter(s).

SUMMARY OF THE INVENTION

This application presents a system and related methods to image and analyze tissue volume for screening and diagnostic purposes. In some embodiments, the system generates acoustic signals by subjecting the tissue volume to a ring transducer setup, computes acoustic properties, such as sound attenuation, of the tissue volume with respect to the acoustic signals, and provides diagnostic information regarding the tissue volume based on the acoustic properties. By generating extensive and systematic acoustic signals via the ring transducer setup, the system can increase the accuracy of computing the acoustic properties of the tissue volume. By modeling sound attenuation in addition to sound speed, the system can further increase the accuracy of the computation and ultimately the effectiveness of generating diagnostic information.

In one aspect, a computer-implemented method of analyzing a volume of tissue is provided in accordance with further aspects of the invention. The method comprises receiving, from a transducer, a set of acoustic signals derived from acoustic waveforms transmitted through the volume of tissue. The transducer comprises an array of ultrasound transmitters and an array of ultrasound receivers configured to surround the volume of tissue. The method further comprises generating a sound speed model that characterizes sound attenuation to represent a distribution of sound speed across a region of the volume of tissue; extracting a set of frequency components from the set of acoustic signals; generating a simulated wavefield in terms of a frequency component and the sound speed model; iteratively refining a value of the sound speed model with respect to the simulated wavefield for each of the set of frequency components until a threshold condition is satisfied, thereby producing a final value of the sound speed model; computing an attenuation representation from the final value of the sound speed model; and rendering one or more images for the volume of tissue based on the attenuation representation.

In some embodiments, generating the simulated wavefield comprises modeling propagation of acoustic waves transmitted through the volume of tissue according to a Helmholtz operation expressed as $[\nabla^2 + \omega^2/c(r)^2]u(r,\omega) = s(r,\omega)$. $\nabla^2$ is the Laplacian operator, and $[\nabla^2 + \omega^2/c(r)^2]$ is a Helmholtz operator, including $\omega$ as a frequency component, c as the sound speed model, u as an expected numerical wavefield obtained at positions r of the transducer for the frequency component $\omega$, and s as a spatial ultrasound source of the transducer.

In some embodiments, generating the sound speed model comprises generating a set of acoustomechanical parameter slices associated with a set of coronal slices through the volume of tissue without considering out-of-plane acoustic waveform scattering.

In some embodiments, the sound attenuation is intrinsic attenuation of a medium.

In some embodiments, the sound speed model is expressed as $c = c_R + ic_I$, where $c_R$ is a real portion corresponding to a phase velocity and $c_I$ is an imaginary portion proportional to the sound attenuation. Then, the refining comprises applying a gradient of an error cost function comprising a difference between the simulated wavefield and a given wavefield. The applying is expressed as $c^2 = c^1 - \beta \nabla S(\omega, c^1)$, where $c^2$ is an updated value of the sound speed model, $c^1$ is a present value of the sound speed model, $\alpha$ is a step size, $\nabla E$ is the gradient of the error cost function, and $\omega$ is one of the set of frequency components. Then, the refining may further comprise applying the gradient with respect to the real portion for one of the set of frequency components to obtain a value for the real portion; applying the gradient with respect to the imaginary portion for the one frequency components using the value for real portion; and proceeding to another of the set of frequency components. Alternatively, the refining may further comprise applying the gradient with respect to the real portion for each of the set of frequency components to obtain a value for the real portion; and applying the gradient with respect to the imaginary portion for each of the set of frequency components using the value for real portion.

In some embodiments, the refining is performed for a lower frequency component before a higher frequency component.

In some embodiments, the method further comprises distributing a total number of iterations to the set of frequency components. The refining is then performed for each of the frequency components for the number of iterations distributed to the frequency component. The number of iterations distributed to a lower of the set of frequencies may be no smaller than a number distributed to a higher of the set of frequencies.

In some embodiments, the sound speed model is expressed as $c=c_R+ic_I$, where $c_R$ is a real portion corresponding to a phase velocity and $c_I$ is an imaginary portion proportional to the sound attenuation. Then, the rendering comprises generating an image based on a final value of the real portion of the sound speed model.

In some embodiments, the sound speed model is expressed as $c=c_R+ic_I$, where $c_R$ is a real portion corresponding to a phase velocity and $c_I$ is an imaginary portion proportional to the sound attenuation. Then, the method further comprises classifying different types of lesions in the volume of tissue based on a final value of the real portion of the sound speed model. The method further comprises refining the classification using the attenuation representation.

In another aspect, a non-transitory computer-readable storage medium with instructions stored thereon that, when executed by a computing system, cause the computing system to perform a method of analyzing a volume of tissue is provided in accordance with further aspects of the invention. The method comprises receiving, from a transducer, a set of acoustic signals derived from acoustic waveforms transmitted through the volume of tissue. The transducer comprises an array of ultrasound transmitters and an array of ultrasound receivers configured to surround the volume of tissue. The method further comprises generating a sound speed model that characterizes sound attenuation to represent a distribution of sound speed across a region of the volume of tissue; extracting a set of frequency components from the set of acoustic signals; generating a simulated wavefield in terms of a frequency component and the sound speed model; iteratively refining a value of the sound speed model with respect to the simulated wavefield for each of the set of frequency components until a threshold condition is satisfied, thereby producing a final value of the sound speed model; computing an attenuation representation from the final value of the sound speed model; and rendering an image for the volume of tissue based on the attenuation representation.

In some embodiments, the method further comprises distributing a total number of iterations to the set of frequency components. The refining is performed for each of the frequency components for the number of iterations distributed to the frequency component. A number of iterations distributed to a lower frequency may be no smaller than a number distributed to a higher frequency.

In some embodiments, the sound model comprises a real portion and an imaginary portion corresponding respectively to a phase velocity and the sound attenuation. The refining comprises applying a gradient of an error cost function with respect to the real portion for one of the set of frequency components to obtain a value for the real portion. The error cost function comprises a difference between the simulated wavefield and a given wavefield. The refining further comprises applying the gradient with respect to the imaginary portion for the one frequency component using the value for real portion, and proceeding to another of the set of frequency components.

In another aspect, a system for analyzing a volume of tissue is provided in accordance with further aspects of the invention. The system comprises a transducer comprising an array of ultrasound transmitters and an array of ultrasound receivers and configured to surround the volume of tissue. The array of ultrasound transmitters emits acoustic waveforms toward the volume of tissue to be received by the array of ultrasound transceivers; and the transducer converts received acoustic waveforms to a set of acoustic signals. The system further comprises a processor, comprising a generating unit configured to generate a sound speed model that characterizes sound attenuation to represent a distribution of sound speed across a region of the volume of tissue; an identifying unit configured to identify a set of frequencies from the set of acoustic signals; a creating unit configured to create a simulated wavefield in terms of a frequency and the sound speed model; a refining unit configured to iteratively refine a value of the sound speed model with respect to the simulated wavefield for each of the set of frequencies until a stop condition is satisfied, thereby producing a final value of the sound speed model; a computing unit configured to compute an attenuation representation from the final value of the sound speed model; and a rendering unit configured to render one or more images for the volume of tissue based on the attenuation representation. The system further comprises a display configured to display the one or more images.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
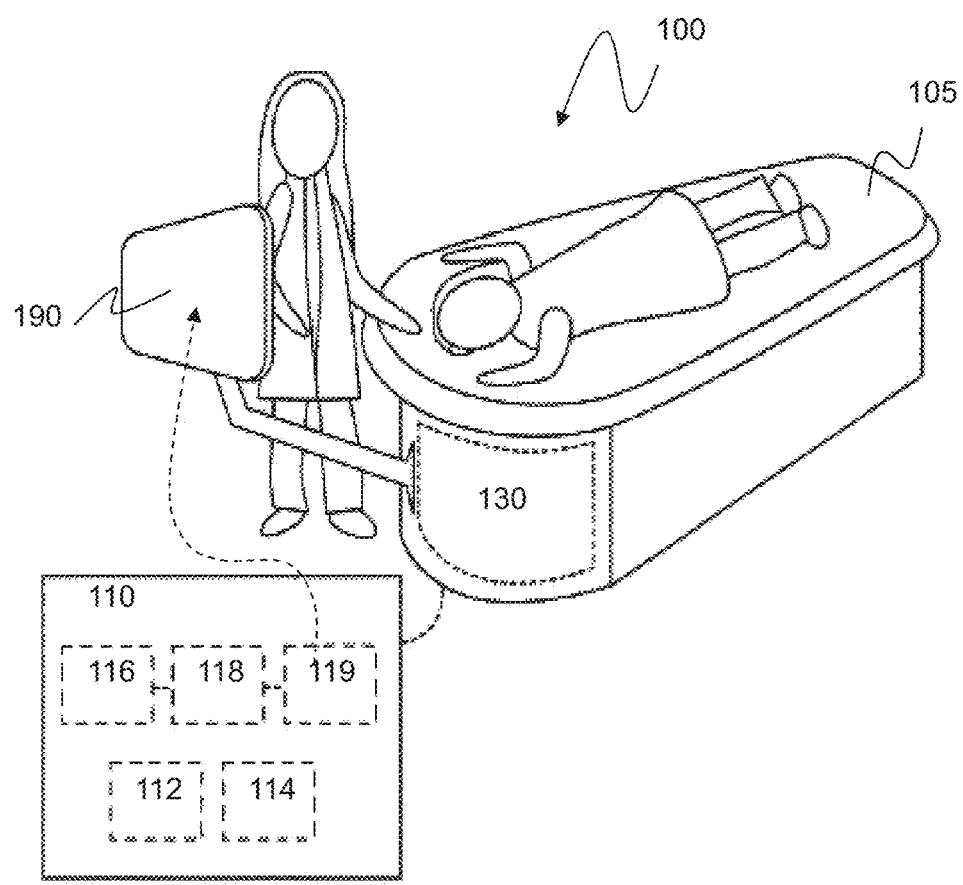
FIGS. 1A-1C illustrate a system for implementing an ultrasound waveform tomography method.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

This application presents a system and related methods that improves tissue imaging for screening and diagnostic purposes. While the discussion below focuses on the breast tissue, the system may be applied to other types of tissue or mass.

Using ultrasound waveform tomography with a ring ultrasound transducer array, a patient can place her breast into the ring transducer array which is submerged in a water filled chamber. Coronal images of the breast are reconstructed after the patient is scanned from the chest wall to the nipple.

In the scanning process, each transducer element of the ring array sequentially acts as a source of ultrasound while all the transducers act as receivers.

To better quantify the sound speed and attenuation properties of a medium, a frequency-domain ultrasound waveform tomography technique is presented in this application. In contrast to ray techniques which use an infinite frequency approximation to the wave equation, frequency-domain waveform tomography techniques more accurately model the physics of wave propagation by accounting for complex wave phenomena such as diffractions and multiple scattering. This has allowed gradient descent inversion algorithms to reconstruct more accurate sound speed and attenuation distributions of the insonified medium by iteratively minimizing a cost function defined as the difference between measured and synthetically generated acoustic pressure fields. By using wave-form tomography techniques, sound speed reconstructions of the breast can give a detailed morphological assessment of the underlying breast disease.

Sound speed and attenuation typically help to differentiate fat, fibro-glandular tissues, benign masses, and malignant cancers. An accurate assessment of these properties can aid in diagnosis by increasing sensitivity and specificity. Although sound speed helps differentiate a variety of tissues in the breast, there is some overlap of the sound speed values of tissues such as cysts, fibroadenomas, and cancers. Attenuation can typically be used to further classify these lesions with similar sound speeds. For example, a fluid filled cyst usually has lower attenuation than a solid mass such as a cancer. By allowing the sound speed to have an imaginary component, waveform tomography techniques can model the intrinsic attenuation of a medium. The intrinsic attenuation of a medium is the energy loss caused by friction that results in heating the medium, which contrasts with energy loss caused by reflections, scattering, and velocity inhomogeneities. The sum of these two types of energy or attenuation, the total attenuation, is typically measured by ray tomography methods. Since the intrinsic attenuation is related to the physical properties of an unknown tissue, it can be used to better characterize and classify lesion types.

The system disclosed in the present application utilizes transmitted ultrasound signal to quantify sound speed and attenuation properties of a breast, based on frequency-domain ultrasound waveform tomography techniques.

Ultrasound Waveform Tomography Apparatus

Figure 1B:
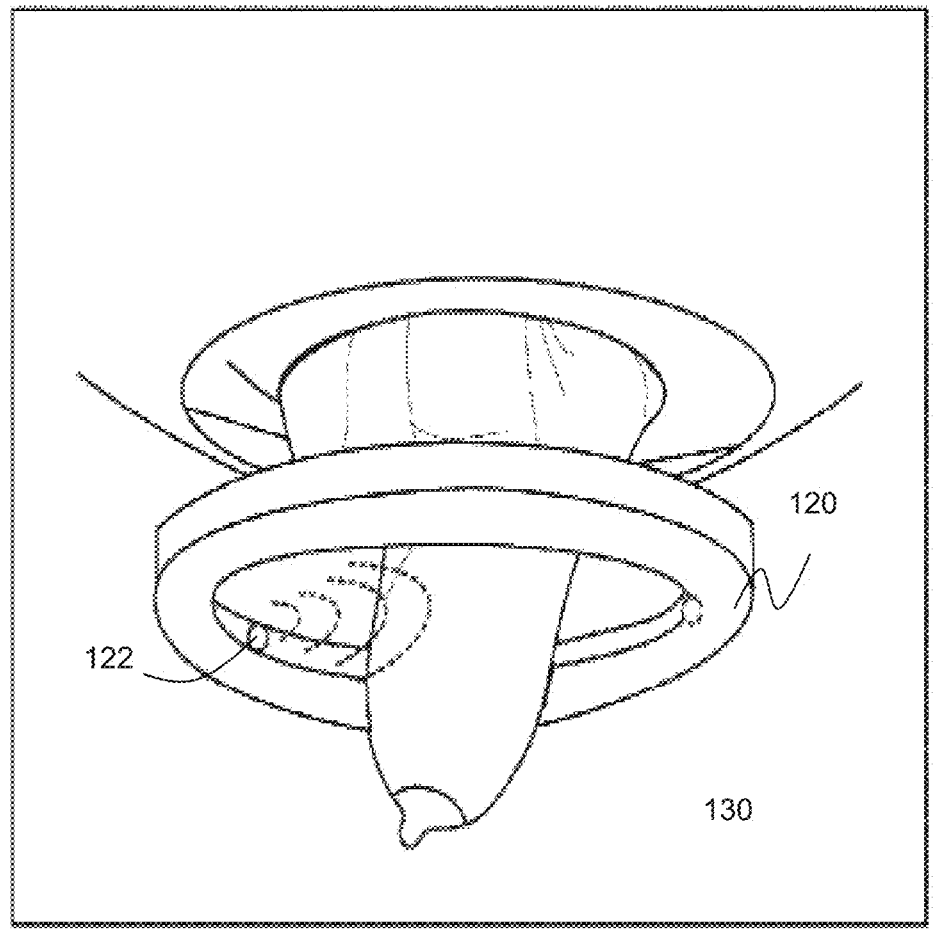
Figure 1C:
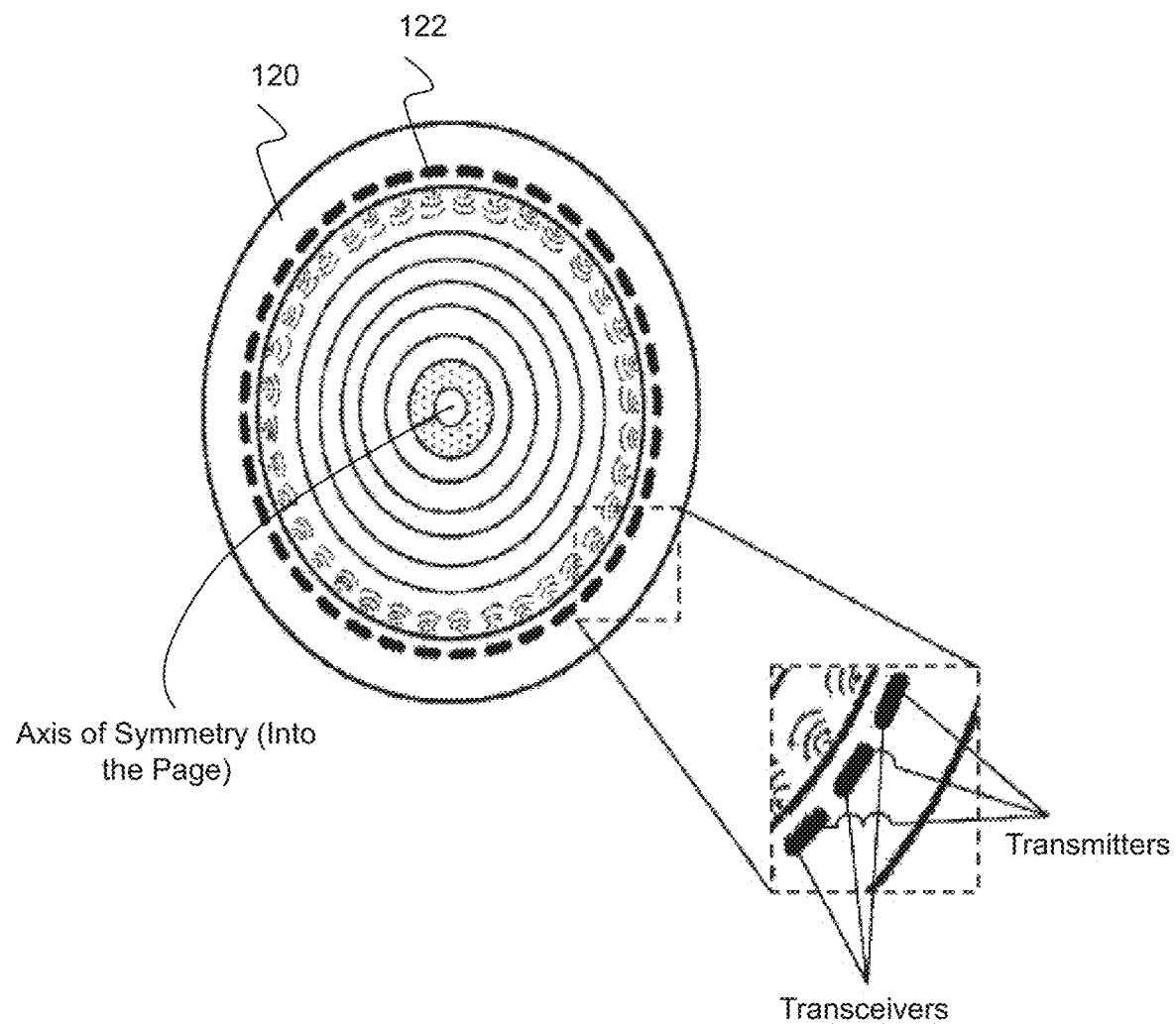

FIGS. 1A-1C illustrate a system for implementing an ultrasound waveform tomography method. As shown in FIGS. 1A-1C, a system 100 for determining a distribution of a stiffness parameter within a volume of tissue comprises: a transducer 120 configured to receive the volume of tissue and comprising an array of ultrasound transmitters and an array of ultrasound receivers, the array of ultrasound transmitters no configured to emit acoustic waveforms toward the volume of tissue and the array of ultrasound receivers configured to detect a set of acoustic signals derived from acoustic waveforms transmitted through the volume of tissue; a computing system 110 in communication with the transducer, the computing system 110 comprising: a first module 112 configured to generate a simulated wavefield model representing a distribution of acoustomechanical parameters, across a region of the volume of tissue and a sound speed model; a second module 114 configured to extract a set of frequency components from the set of acoustic signals; a third module 116 configured to iteratively refine the sound speed model value with respect to the simulated wavefield for each of the frequency components; a fourth module configured to compute a representation of one of the acoustomechanical parameters based on the final model value; and a fifth module 119 configured to generate an enhanced image from the final model value for each of the frequency components; and a display 190 in communication with the computing system 110 and configured to render the enhanced image of the volume of tissue.

The system 100 functions to render ultrasound images and/or generate transformed ultrasound data that can be used to generate a high-resolution image of structures present within a volume of tissue. In some embodiments, the system 100 can function to produce images that are aligned with regulatory standards for medical imaging, as regulated, for instance, by the U.S. Food and Drug Administration (FDA). The system 100 is preferably configured to implement at least a portion of an embodiment or variation described in this application; however, the system 100 can additionally or alternatively be configured to implement any other suitable method.

The transducer 120, the computer processor 110, and the display 190 are preferably coupled to a scanner table 105, as shown in FIGS. 1A and 1B, wherein the scanner table 105 has an opening 106 that provides access to the volume of tissue 10 of the patient. The table, which may be made of a durable, flexible material (e.g., flexible membrane, fabric, etc.), preferably contours to the patient's body, thereby increasing scanning access to the axilla regions of the breast and increasing patient comfort. The opening 106 in the table allows the breast (or other appendage) to protrude through the table and be submerged in an imaging tank 130 filled with water or another suitable fluid as an acoustic coupling medium that propagates acoustic waves.

As shown in FIGS. 1B and 1C, a ring-shaped transducer 120 with transducer elements 122 can be located within the imaging tank 130 and encircle or otherwise surround the breast, wherein each of the transducer elements 122 can comprise one of the array of ultrasound transmitters paired with one of the array of ultrasound receivers. Multiple ultrasound transmitters that direct safe, non-ionizing ultrasound pulses toward the tissue, and multiple ultrasound receivers that receive and record acoustic signals scattering from the tissue and/or transmitted through the tissue, are distributed around the ring transducer 120. In one configuration, the transducer 120 can be organized such that each ultrasound transmitter element is paired with a corresponding ultrasound receiver element, each ultrasound transmitter element is surrounded by two adjacent ultrasound transmitter elements, each ultrasound receiver element is surrounded by two adjacent ultrasound receiver elements, and the transducer is axially symmetric, as in FIG. 1C. During the scan, the ring transducer 120 passes along the tissue, such as in an anterior-posterior direction between the chest wall and the nipple region of the breast to acquire an acoustic data set including measurements such as acoustic reflection, acoustic attenuation, and sound speed, preferably at discrete scanning steps, or coronal "slices". The transducer 120 can be configured to scan step-wise in increments from the chest wall towards the nipple, and/or from the nipple towards the chest wall. However, the transducer 120 may additionally and/or alternatively receive data regarding any suitable biomechanical property of the tissue during the scan, and in any suitable direction.

In some embodiments, the scanner table can comprise an embodiment, variation, or example of the patient interface system described in U.S. application Ser. No. 14/208,181 entitled "Patient Interface System" and filed on 13 Mar. 2014, which is hereby incorporated in its entirety by this reference. Furthermore, in a specific example, the system 100 can implement a ring transducer 120 having 2048 transducer elements in cooperation with an ultrasound tomographic scanner 100 having 512 receive channels, 512 transmit channels, an operating frequency of 3 MHz, a data resolution of 14 bits, an image resolution of 0.7 mm, a slice thickness of 2.5 mm, a reconstruction time per slice of 15 seconds, and an ability to accommodate volumes of tissue 22 cm in diameter. However, system 100 can additionally or alternatively comprise or be coupled with any other suitable patient interface system.

The computing system 110 can be implemented at least in part in the cloud and/or as a machine (e.g., computing machine, server, etc.) configured to receive computer-readable instructions. Additionally or alternatively, the computer processor can be implemented on one or more computer networks, computer systems, or applications servers, etc., wherein the computer system(s) can comprise one or more of: a cloud-based computer, a mainframe computer system, a grid-computer system, or any other suitable computer system. In one variation, the first module 112, the second module 114, the third module 116, the fourth module 118, and the fifth module 119 of the computing system 110 are implemented as software modules executing on a computer machine coupled to the scanner table 105 and in communication with the display 190; however, the computing system 110 can additionally or alternatively be implemented using any other suitable computing system architecture.

The system 100 can include any other suitable elements that facilitate detection, processing, and/or analyzing of acoustic signals generated from a volume of tissue of the user in a manner that provides a representation of stiffness within the volume of tissue. Furthermore, as a person skilled in the art will recognize from the previous detailed description and from the figures and claims, modifications and changes can be made to the preferred embodiments of the system 100 without departing from the scope of system 100.

Frequency-Domain Waveform Computation

In the typical diagnostic range of 0.5-10 MHz, the acoustic attenuation of ultrasound waves in soft tissue is approximately linearly dependent on the frequency. In some embodiments, for soft tissues, it is assumed that there is no dispersion of the acoustic phase velocity. To model attenuation due to ultrasound energy losses, i.e., the intrinsic attenuation, the computing system allows the sound speed model to have an imaginary component: $c=c_R+ic_I$, where $c_R$ represents the phase velocity and $c_I$ is proportional to the attenuation. The computing system updates the sound speed distribution a configurable number of times for a particular frequency and proceeds to the next frequency of interest to begin updating again. In this manner, a sound speed image is gradually improved at a finer scale until the end of the reconstruction process.

Figure 2:
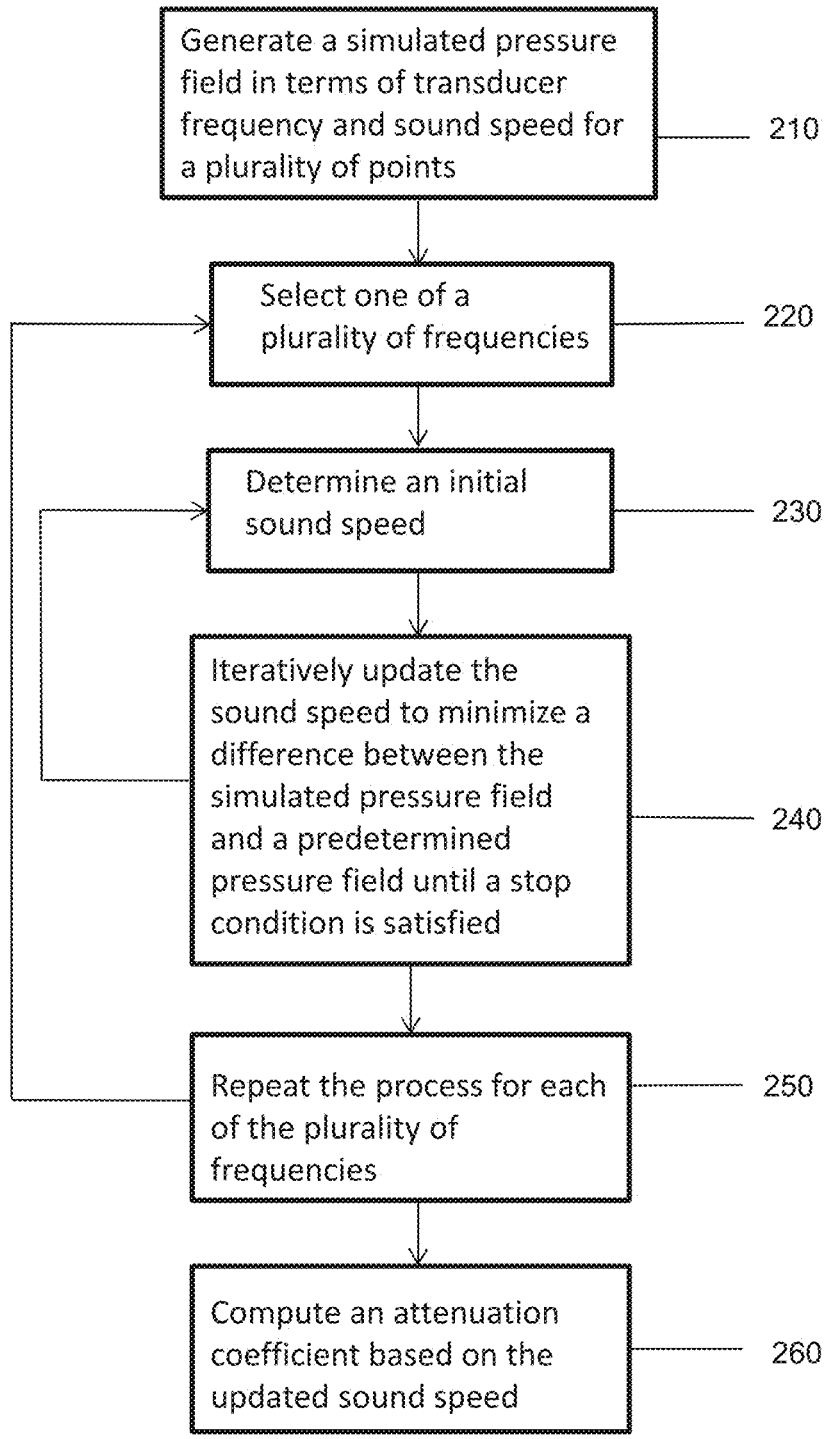
FIG. 2 illustrates an example process of determining sound attenuation and generating a corresponding tissue image using frequency-domain waveform tomography.

FIG. 2 illustrates an example process of determining sound attenuation and generating a corresponding tissue image using frequency-domain waveform tomography. In some embodiments, initially, the computing system identifies a set of frequencies from the set of acoustic signals, which are typically in the range of 0.5-10 MHz. In step 210, the computing system generates a simulated acoustic pressure field in terms of frequency and sound speed for a slice of the given tissue, but the simulated pressure field can include other acousticmechanical parameters, such as density, compressibility, reflectivity, absorption, or acoustic impedance. The computing system can generate the simulated pressure field by solving the Helmholtz equation for a complex sound speed model c and frequency component $\omega$, thereby creating forward modeled pressure field data $u_{obs}(\omega,$ c). Solutions to the Helmholtz equation ignore generally viscosity and only decrease in amplitude due to geometrical spreading. Solving the Helmholtz equation can be accomplished by using finite difference methods to model the Helmholtz operator using a matrix representation $$\left(\nabla^2 + \frac{\omega^2}{c^2}\right)u_{obs}(\omega, c) = f(\omega) \longleftrightarrow Su = f,$$

where $\nabla^2$ is the Laplacian operator, $f(\omega)$ is the source function, S is the matrix representation of the Helmholtz operator, u is the quantized forward modeled pressure field, and f is the quantized source function.

In steps 220-250, the computing system iteratively updates the value of the sound speed model to reduce the value of an error cost function discussed below for each of the identified frequencies. In step 220, the computing system selects one of the identified frequencies. Typically, lower frequencies are considered before higher frequencies, although an appropriate selection of an initial frequency may allow more flexibility in the selection of the subsequent frequencies. In step 230, for the selected frequency, the computing system selects an initial sound speed, as further discussed below.

In step 240, the computing system iteratively updates the sound speed to minimize the difference between the simulated pressure field value and a predetermined pressure field until a stop condition is satisfied. In some embodiments, after solving the resultant system of equations for the forward modeling pressure field data $u_{obs}(\omega,$ c), the computing system creates the data residual mismatch $e(\omega,$ c) defined as the difference between $u_{obs}(\omega,$ c) and a real pressure field data $d_{obs}(\omega)$.

$$e(\omega,c)=u_{obs}(\omega,c)-d_{obs}(\omega).$$

The real pressure field data $d_{obs}(\omega)$ can be obtained by extracting $f(\omega)$ of the ultrasound waveform for each given ultrasound transmitter/receiver pair. Specifically, this can be achieved by applying a time domain window on the waveform, computing its Fourier transform, and selecting the desired frequency.

In some embodiments, each frequency gives a unique vector $d_{obs}(\omega)$. Gradient descent methods can then be used to minimize a real valued mean squared error cost function $S(\omega,$ c) defined as the inner product of the data residual mismatch $$S(w,c)=\tfrac{1}{2}e^H(w,c)e(w,c),$$

where $^H$ denotes the Hermitian transpose. By taking the gradient of the cost function, the computing system obtains an update equation for the real or imaginary part of the sound speed model $$*c^{(i+1)}=c^{(i)}-\beta\nabla S(w,c^{(i)}),$$

where the step size $\beta$ is chosen by either line search or a step size approximation method and $\nabla=\partial/\partial c_R$ or $\partial/\partial c_I$ depending on whether it is the real or imaginary part of the sound speed model that is being updated. The computing system can repeat this iterative process until a specific condition is satisfied.

In some embodiments, the computing system determines the real part and the imaginary part of the sound speed model in a configurable manner. Typically, the computing system focuses on the real part of the sound speed model initially by assuming that the imaginary part does not exist or is a constant. Once the real part is determined, the computing system can reintroduce the imaginary part into the sound speed model. The computing system can compute the real part for a current frequency and subsequently compute the imaginary part for the same frequency, before moving on to the next frequency. In that case, once the last $c_R^{i+1}$, $c'_R$, is determined for the current frequency, the computing system obtains $c^{i+1}$ in the starred equation with $c_R^i$ equal to $c'_R$ and $\nabla = \partial/\partial c_I$ for every i. The result for the current frequency can be used as the initial value for the next frequency. The system can also compute the real part for all the frequencies before computing the imaginary part for all the frequencies. In that case, once the last $c'_R$ is determined for the last frequency, the computing system obtains $c^{i+1}$ in the starred equation with $c_R^i$ equal to the last $c'_R$ and $\nabla = \partial/\partial c_I$ for every i. It is to be appreciated by someone of ordinary skill in the art that the real part and the imaginary part for different frequencies can be computed in other sequences.

In some embodiments, the computing system determines the number of iterations to carry out for each frequency in a configurable manner. The computing system can assign a specific step size to each frequency. The computing system can also assign a threshold such that the specific condition is that the current value of the real part or the imaginary part or the difference from the previous value is less than the threshold. In addition, tests and experiments have shown that the symmetric nature of the ring configuration tends to lead to relatively stable results, including that the total number of iterations over all the frequencies that is required to obtain a high-accuracy sound speed or a high-quality image tends to be stable. Therefore, the computing system can mainly control the total number of iterations over all the frequencies and then distribute that to the different frequencies. Generally, the gradient descent process can be performed for lower frequencies with lower computational requirements than higher frequencies. Therefore, the computing system can distribute larger numbers of iterations to lower frequencies to reduce the overall computational requirements. There can be a change in the number of iterations from one frequency to the next, or the number of frequencies can change step-wise, being constant for several frequencies at a time. Similar or different total numbers of iterations can be used for the real part and the imaginary part, and similar or different distributions can be used for the real part and the imaginary part. It is to be appreciated by someone of ordinary skill that the number of iterations for each frequency can be determined in additional ways that are conducive to efficient resource utilization and effective output production. Referring back to FIG. 2, in step 250, the computing system then repeats the process for each of the identified frequencies.

In step 260, the computing system computes an attenuation coefficient based on the updated, final value of the sound speed model. In some embodiments, a frequency independent quality factor Q that relates energy losses to the real and imaginary sound speed is defined in terms of the energy loss $\Delta E$ in a cycle of a plane wave oscillating at frequency w $$\frac{1}{Q} = -\frac{\Delta E}{2\pi E}.$$

In some embodiments, the amplitude A(x) at a position x of a plane wave with initial amplitude $A_0$ oscillating at a frequency w in a medium with the sound speed model $c = c_R + ic_I$ and quality factor Q can be given by $$A(x) = A_0 \exp\left[\frac{-\omega x}{2c_R Q}\right],$$

$$c_I = \frac{c_R}{2Q},$$

The ultrasound attenuation coefficient α, which has units of dB/(mm·MHz), can then be given by $$A(x) = A_0 \exp[-\alpha x],$$

$$\alpha = \frac{20}{\ln 10} \frac{2\pi c_I}{c_R^2}.$$

Tissue Volume Imaging

In some embodiments, the computed value of the sound speed model can be plotted for easy visualization of the tissue structure. For a test of the in vivo capability of the frequency-domain waveform tomography attenuation algorithm, a heterogeneous tissue mimicking breast phantom is used. The tissue mimicking phantom simulates breast tissue and disease, comprised of a bulk glandular tissue center which is surrounded by a subcutaneous fat layer that is further enveloped by a thin skin layer. Embedded within the glandular tissue are different lesions with varying sound speed and attenuation characteristics which simulate cancers, cysts, and fibroadenomas. The phantom reconstructions used frequencies between 500 and 1010 kHz with a frequency interval of 30 kHz. Two ring array transducers with 1024 transducer elements and central frequencies of 2.5 MHz were used to acquire the data for the tissue mimicking phantom. The inversions used the ray tomography sound speed model as an initial sound speed model and a constant attenuation coefficient of 0.1 dB/(mm·MHz) for the initial attenuation model.

Figure 3:
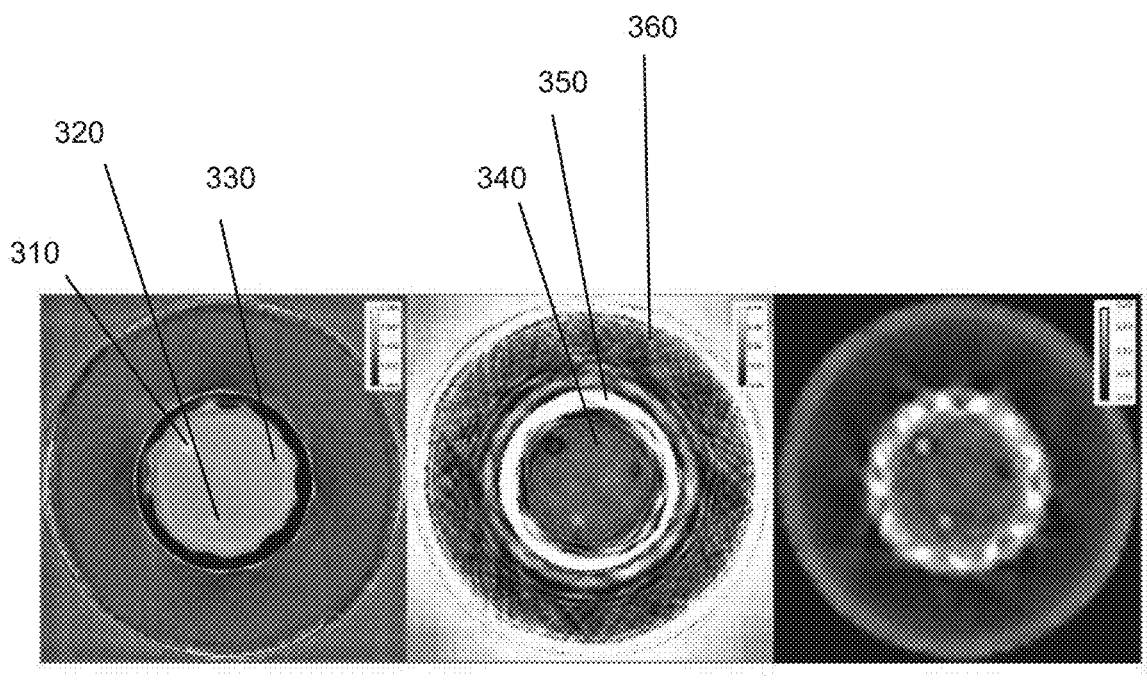
FIGS. 3A-3C illustrate a reconstruction of a tissue mimicking heterogeneous breast phantom.

FIGS. 3A-3C illustrates a reconstruction of the tissue mimicking heterogeneous breast phantom. FIG. 3A illustrates an image corresponding to the reconstructed waveform sound speed, typically the real part of the sound speed formulation, with an overlay bar in units of mm/μs. FIG. 3B illustrates an image corresponding to the reconstructed waveform attenuation coefficient, with an overlay bar in units of dB/(mm·MHz). FIG. 3C illustrates an image corresponding to the ray attenuation with an overlay bar in units of dB/mm. From the sound speed image in FIG. 3A, it can be seen that the system is able to recover the central glandular tissue layer 330, the surrounding subcutaneous fat layer 340, the outer skin layer 350, and three embedded lesions mimicking a cyst 310 (10 o'clock), a fibroadenoma 330 (2 o'clock), and a cancer 320 (6 o'clock). There is correlation between the waveform attenuation and sound speed images. The locations of the three lesions are well correlated between the images, and the fact that the central glandular tissue layer 330 is surrounded by a layer of different material is also visualized within the attenuation image. These correlations are not just a result of the cross talk within the parameter space of complex sound speed. This is seen by viewing the cyst 310 and cancer 320 which both show up as higher sound speed objects but have lower and higher attenuation values, respectively.

The comparison of the waveform attenuation image to the ray attenuation image shows promise for the validity of the waveform attenuation method. It can be seen that the location and polarity of the three lesions are concordant as well as the relative contrast between the inner glandular tissue layer 330 and surrounding subcutaneous fat layer 340. In particular, the ideally low attenuation cyst 310, which is visualized as a high attenuation object with a low attenuation halo surrounding it in the ray based image, is converted to a fairly uniform low attenuation object within the waveform inversion process. One issue seen in both the waveform and ray attenuation reconstructions is the imaging of the fat glandular interface. Due to an impedance mismatch between the layers, reflections obscure the ability to image the interface within the attenuation parameter space. This results in the recovery of a false high attenuation fat layer 340 when it should ideally be low attenuation. However, this issue affects the reconstructed numerical values of the interface region and not the visualization of the interface boundary and skin layer. The interface boundary and skin layer can be visualized well in FIG. 3B if the contrast is modified. The reconstructed waveform attenuation values of the tissue mimicking phantom are plausible and might be indicative of the truth. Since the tissue mimicking phantom was scanned by an ultrasound array with a central frequency of 2.5 MHz, dividing FIG. 3C by 2.5 would convert it the same unit scale used in FIG. 3B. With this conversion, the attenuation values of the two attenuation images are relatively the same. Although, one would still expect the total attenuation ray image to have higher overall attenuation since it accounts for both intrinsic and scattering attenuation.

By comparing the measured waveform sound speed and attenuation values to the specifications reported by the manufacturer, it appears that to a large degree, the reconstructed sound speed values agree with the manufacturer. Care should be taken, however, for smaller lesions which may have yet to fully converge and whose numerical values are skewed from the effects of partial volume averaging of adjacent tissue with lower sound speed. For the attenuation reconstructions, there appears to be a partial agreement with the reported values, which is a significant improvement over reconstructions previously produced by other systems. It is possible that utilizing ultrasound transducers with more suitable central frequencies will further improve the accuracy of the attenuation reconstruction.

Computer Systematization

Figure 4:
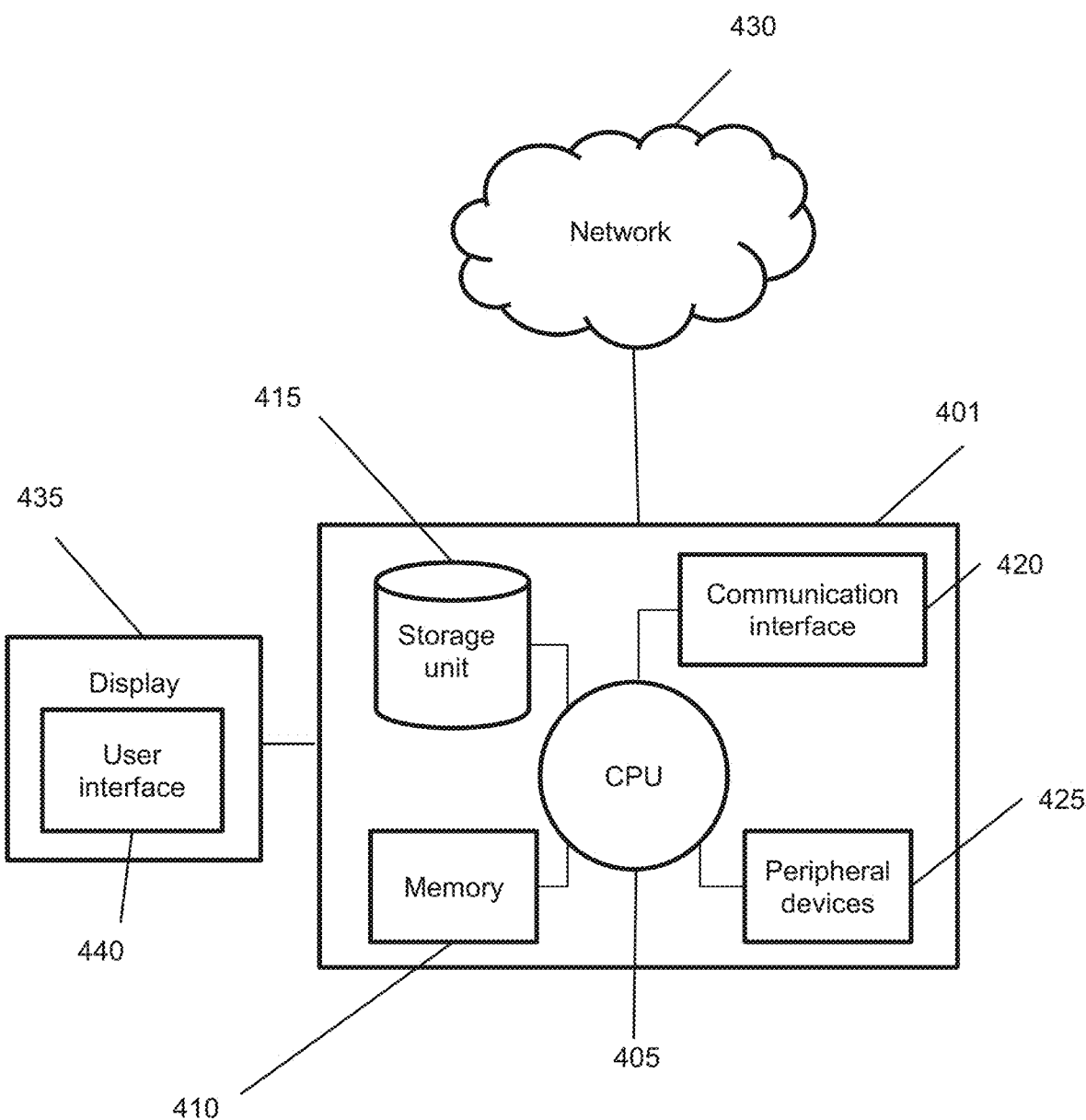
FIG. 4 illustrates a computer system that can be configured to implement any computing system disclosed in the present application.

FIG. 4 shows a computer system 401 that can be configured to implement any computing system disclosed in the present application. The computer system 401 can comprise a mobile phone, a tablet, a wearable device, a laptop computer, a desktop computer, a central server, etc.

The computer system 401 includes a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the system 401 can be included in the circuit. In some cases, the circuit is an application specific integrated circuit (ASIC).

The storage unit 415 can store files, such as drivers, libraries and saved programs. The storage unit 415 can store user data, e.g., user preferences and user programs. The computer system 401 in some cases can include one or more additional data storage units that are external to the computer system 401, such as located on a remote server that is in communication with the computer system 401 through an intranet or the Internet.

The computer system 401 can communicate with one or more remote computer systems through the network 430. For instance, the computer system 401 can communicate with a remote computer system of a user. Examples of remote computer systems include personal computers, slate or tablet PC's, smart phones, personal digital assistants, and so on. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface 440 for providing, for example, a management interface. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 405.

CONCLUSION

In addition to the above mentioned examples, various other modifications and alterations of the invention may be made without departing from the invention. Accordingly, the above disclosure is not to be considered as limiting, and the appended claims are to be interpreted as encompassing the true spirit and the entire scope of the invention.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

What is claimed is:

1. A computer-implemented method of analyzing a volume of tissue, comprising:
    receiving, from a transducer, a set of acoustic signals derived from acoustic waveforms transmitted through the volume of tissue,
    wherein the transducer comprises an array of ultrasound transmitters and an array of ultrasound receivers configured to surround the volume of tissue;
    generating a sound speed model that characterizes sound attenuation to represent a distribution of sound speed across a region of the volume of tissue;
    extracting a set of frequency components from the set of acoustic signals;
    distributing a total number of iterations to the set of frequency components;
    generating a simulated wavefield in terms of a frequency component of the set of frequency components and the sound speed model;
    iteratively refining a value of the sound speed model with respect to the simulated wavefield for each of the set of frequency components until a threshold condition is satisfied, thereby producing a final value of the sound speed model, wherein the refining is performed for each of the frequency components for the number of iterations distributed to the frequency component, wherein a number of iterations distributed to a lower of the set of frequencies is no smaller than a number distributed to a higher of the set of frequencies;
    computing an attenuation representation from the final value of the sound speed model; and
    rendering one or more images for the volume of tissue based on the attenuation representation.

2. The method of claim 1,
    wherein generating the simulated wavefield comprises modeling propagation of acoustic waves transmitted through the volume of tissue according to a Helmholtz operation expressed as $[\nabla^2+\omega^2/c(r)^2]u(r,\omega)=s(r,\omega)$,
        wherein $\nabla^2$ is the Laplacian operator, and $[\nabla^2+\omega^2/c(r)^2]$ is a Helmholtz operator, including $\omega$ as a frequency component, c as the sound speed model, u as an expected numerical wavefield obtained at positions r of the transducer for the frequency component ω, and s as a spatial ultrasound source of the transducer.

3. The method of claim 1, wherein generating the sound speed model comprises generating a set of acoustomechanical parameter slices associated with a set of coronal slices through the volume of tissue without considering out-of-plane acoustic waveform scattering.

4. The method of claim 1, wherein the sound attenuation is intrinsic attenuation of a medium.

5. The method of claim 1, wherein the refining is performed for the lower of the set of frequencies before the higher of the set of frequencies.

6. The method of claim 1,
wherein in the sound speed model is expressed as $c=c_R+ic_I$,
wherein $c_R$ is a real portion corresponding to a phase velocity and $c_I$ is an imaginary portion proportional to the sound attenuation.

7. The method of claim 6, wherein the rendering comprises generating an image based on a final value of real portion of the sound speed model.

8. The method of claim 6, further comprising classifying different types of lesions in the volume of tissue based on a final value of real portion of the sound speed model.

9. The method of claim 8, further comprising refining the classification using the attenuation representation.

10. The method of claim 6, wherein the refining comprises applying a gradient of an error cost function comprising a difference between the simulated wavefield and a given wavefield.

11. The method of claim 10,
wherein the applying is expressed as $c^2=c^1-\beta \nabla S(\omega,c^1)$,
wherein $c^2$ is an updated value of the sound speed model, $c^1$ is a present value of the sound speed model, $\beta$ is a step size, $\nabla S$ is the gradient of the error cost function, and $\omega$ is one of the set of frequency components.

12. The method of claim 10, wherein the refining comprises:
applying the gradient with respect to real portion for one of the set of frequency components to obtain a value for the real portion;
applying the gradient with respect to imaginary portion for the one frequency components using the value for the real portion; and
proceeding to another of the set of frequency components.

13. The method of claim 10, wherein the refining comprises:
applying the gradient with respect to real portion for each of the set of frequency components to obtain a value for the real portion; and
applying the gradient with respect to imaginary portion for each of the set of frequency components using the value for the real portion.

14. A non-transitory computer-readable storage medium with instructions stored thereon that, when executed by a computing system, cause the computing system to perform a method of analyzing a volume of tissue, the method comprising:
receiving, from a transducer, a set of acoustic signals derived from acoustic waveforms transmitted through the volume of tissue,
wherein the transducer comprises an array of ultrasound transmitters and an array of ultrasound receivers configured to surround the volume of tissue;
generating a sound speed model that characterizes sound attenuation to represent a distribution of sound speed across a region of the volume of tissue;
extracting a set of frequency components from the set of acoustic signals;
distributing a total number of iterations to the set of frequency components;
generating a simulated wavefield in terms of a frequency component of the set of frequency components and the sound speed model;
iteratively refining a value of the sound speed model with respect to the simulated wavefield for each of the set of frequency components until a threshold condition is satisfied, thereby producing a final value of the sound speed model, wherein the refining is performed for each of the frequency components for the number of iterations distributed to the frequency component, wherein a number of iterations distributed to a lower frequency is no smaller than a number distributed to a higher frequency;
computing an attenuation representation from the final value of the sound speed model; and
rendering an image for the volume of tissue based on the attenuation representation.

15. The non-transitory computer-readable storage medium of claim 14,
wherein the sound speed model comprises a real portion and an imaginary portion corresponding respectively to a phase velocity and the sound attenuation, and
wherein the refining comprises:
applying a gradient of an error cost function with respect to real portion for one of the set of frequency components to obtain a value for the real portion,
wherein the error cost function comprises a difference between the simulated wavefield and a given wavefield,
applying the gradient with respect to imaginary portion for the one frequency component using the value for real portion, and
proceeding to another of the set of frequency components.

16. A system for analyzing a volume of tissue, comprising:
a transducer comprising an array of ultrasound transmitters and an array of ultrasound receivers and configured to surround the volume of tissue,
wherein the array of ultrasound transmitters emits acoustic waveforms toward the volume of tissue to be received by the array of ultrasound receivers; and
wherein the transducer converts received acoustic waveforms to a set of acoustic signals;
a processor, comprising:
a generating unit configured to generate a sound speed model that characterizes sound attenuation to represent a distribution of sound speed across a region of the volume of tissue;
an identifying unit configured to identify a set of frequencies from the set of acoustic signals;
a distributing unit configured to distribute a total number of iterations to the set of frequencies;
a creating unit configured to create a simulated wavefield in terms of a frequency of the set of frequencies and the sound speed model;
a refining unit configured to iteratively refine a value of the sound speed model with respect to the simulated wavefield for each of the set of frequencies until a stop condition is satisfied, thereby producing a final value of the sound speed model, wherein refining is performed for each of the frequencies for the number of iterations distributed to the set of frequencies, wherein a number of iterations distributed to a lower of the set of frequencies is no smaller than a number distributed to a higher of the set of frequencies;

a computing unit configured to compute an attenuation representation from the final value of the sound speed model; and a rendering unit configured to render one or more images for the volume of tissue based on the attenuation representation; and a display configured to display the one or more images.

* * * * *